US008981296B2

(12) United States Patent
Cox et al.

(10) Patent No.: US 8,981,296 B2
(45) Date of Patent: Mar. 17, 2015

(54) TERAHERTZ DISPERSIVE SPECTROMETER SYSTEM

(75) Inventors: James A. Cox, New Brighton, MN (US); Bernard S. Fritz, Eagan, MN (US); Fouad Nusseibeh, Champlin, MN (US)

(73) Assignee: Honeywell International Inc., Morristown, NJ (US)

( * ) Notice: Subject to any disclaimer, the term of this patent is extended or adjusted under 35 U.S.C. 154(b) by 283 days.

(21) Appl. No.: 13/367,209

(22) Filed: Feb. 6, 2012

(65) Prior Publication Data
US 2012/0199743 A1  Aug. 9, 2012

Related U.S. Application Data

(63) Continuation-in-part of application No. 11/935,917, filed on Nov. 6, 2007, now abandoned.

(51) Int. Cl.
*G01J 5/00* (2006.01)
*G01J 5/02* (2006.01)
*G01J 5/08* (2006.01)
*G01J 5/10* (2006.01)
*G01J 3/42* (2006.01)
*G01N 21/3581* (2014.01)
*G01N 21/3563* (2014.01)
*G01N 21/3577* (2014.01)

(52) U.S. Cl.
CPC ............... *G01J 3/42* (2013.01); *G01N 21/3581* (2013.01); *G01J 5/0837* (2013.01); *G01N 21/3563* (2013.01); *G01N 21/3577* (2013.01)
USPC .................... 250/338.1; 250/338.4; 257/432; 338/18

(58) Field of Classification Search
CPC ...... G01J 3/42; G01J 5/0837; G01N 21/3581; G01N 21/3563; G01N 21/6577
USPC ................ 250/338.4, 338.1; 257/432; 338/18
See application file for complete search history.

(56) References Cited

U.S. PATENT DOCUMENTS

| | | |
|---|---|---|
| 4,636,074 A | 1/1987 | Levy et al. |
| 5,171,733 A | 12/1992 | Hu |
| 5,220,188 A | 6/1993 | Higashi et al. |

(Continued)

OTHER PUBLICATIONS

Mittleman et al., "Gas Sensing Using Terahertz Time-Domain Spectroscopy," Applied Physics B, vol. 67, Laser and Optics, published 1998, pp. 379-390; Retrieved from Internet [May 21, 2014]; Retrieved from url <http://www.ece.rice.edu/~daniel/papers/gas-sensing.pdf>.*

(Continued)

*Primary Examiner* — Yara B Green
(74) *Attorney, Agent, or Firm* — Seager Tufte & Wickhem LLC

(57) ABSTRACT

A spectrometer system for providing information about a target with terahertz radiation. The system may receive incident radiation from the target through fore optics, a slit aperture, secondary optics and a dispersive element which images a slit on an array of terahertz sensitive detectors. The detectors may include uncooled sensors. Each sensor may be connected to its own micro antenna. The array of detectors may be situated proximate to the dispersive element so that radiation from the element may be dispersed according to wavelength to the respective detectors optimally sensitive to the various respective wavelengths. Detector signals indicating the impingement of terahertz radiation may provide information for identifying a material of the target.

10 Claims, 20 Drawing Sheets

(56) References Cited

U.S. PATENT DOCUMENTS

| | | | |
|---|---|---|---|
| 5,220,189 | A | 6/1993 | Higashi et al. |
| 5,449,910 | A | 9/1995 | Wood et al. |
| 5,534,111 | A | 7/1996 | Hocker et al. |
| 5,895,233 | A | 4/1999 | Higashi et al. |
| 6,036,872 | A | 3/2000 | Wood et al. |
| 6,242,740 | B1 | 6/2001 | Luukanen et al. |
| 6,288,781 | B1 | 9/2001 | Lobb |
| 6,392,233 | B1 | 5/2002 | Channin et al. |
| 7,488,940 | B2 | 2/2009 | Ohtake et al. |
| 2003/0071215 | A1 | 4/2003 | Ajisawa |
| 2004/0140429 | A1 | 7/2004 | Jack et al. |
| 2004/0155665 | A1* | 8/2004 | Arnone et al. ............... 324/644 |
| 2004/0156048 | A1 | 8/2004 | Mitchell et al. |
| 2004/0227940 | A1 | 11/2004 | Mitchell |
| 2005/0018201 | A1 | 1/2005 | De Boer et al. |
| 2005/0178952 | A1* | 8/2005 | Wood .................. 250/214 R |
| 2006/0219922 | A1 | 10/2006 | Watanabe et al. |
| 2007/0146720 | A1 | 6/2007 | Cox et al. |
| 2007/0278407 | A1* | 12/2007 | Wood et al. ............... 250/341.1 |
| 2008/0156991 | A1 | 7/2008 | Hu et al. |
| 2009/0114822 | A1 | 5/2009 | Cox et al. |

OTHER PUBLICATIONS

Dietlein et al., "Broadband THz Aqueous Blackbody Calibration Source," Proc. SPIE 6548, Pasive Millimeter-Wave Imaging Technology X, 65480M, published May 1, 2007; doi:10.1117/12.720165. Retrieved from Internet [May 21, 2014]; Retrieved from url <https://proceedings.spiedigitallibrary.org/proceeding.aspx?articleid=1338455>.*

All non-patent literature previously provided in parent U.S. Appl. No. 11/935,917, filed Nov. 6, 2007.

Conn, G.K.T., "A Thermocouple-Bolometer Detector," University of Sheffield Physics Department, Nov. 1944.

Bell, "Lamellar Grating Interferometers," Introductory Fourier Transform Spectroscopy, Chapter 15, pp. 200-230. 1972.

Grossman et al., "Terahertz Active Direct Detection Imagers," Terahertz for Military and Security Applications II, Proceedings of SPIE vol. 5411, pp. 68-77, 2004.

Manzardo et al., "Miniature lamellar grating interferometer based on silicon technology," Optical Society of America, vol. 29, No. 18, pp. 1437-1439, Jul. 1, 2004.

Miller et al., "Micromaohined antenna-coupled uncooled microbolometers for terahertz imaging arrays," Terahertz for military and Security Applications II, Proceedings of SPIE vol. 5411, pp. 18-24, 2004.

Strong, "Interferometry for the Far Infrared," Journal of the Optical Society of America, vol. 47, No. 5, pp. 354-357, May 1957.

* cited by examiner

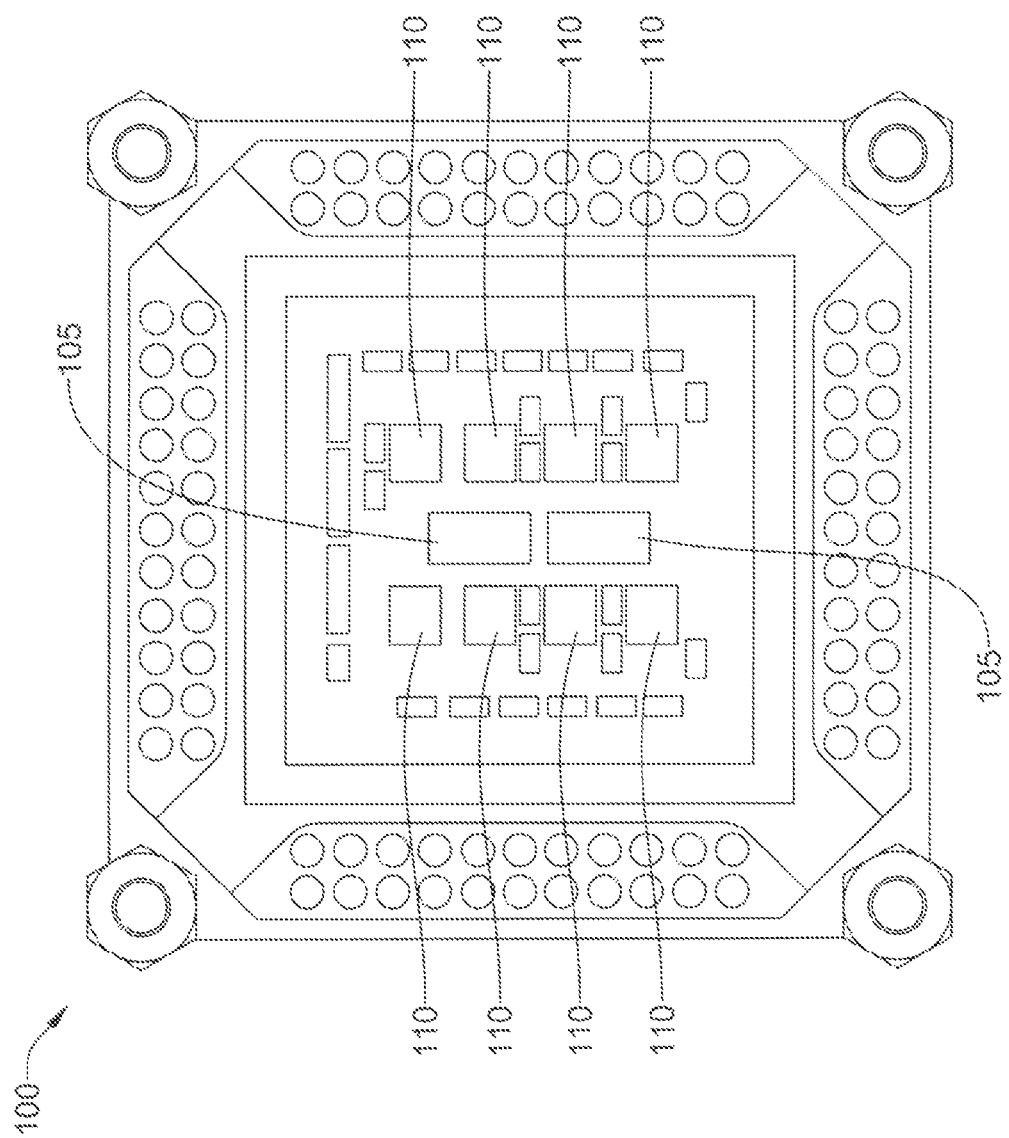

TERAHERTZ DISPERSIVE SPECTROMETER SYSTEM

This application is a continuation-in-part of U.S. patent application Ser. No. 11/935,917, filed Nov. 6, 2007, and entitled "Terahertz Dispersive Spectrometer System." U.S. patent application Ser. No. 11/935,917, filed Nov. 6, 2007 is hereby incorporated by reference.

BACKGROUND

The present disclosure pertains to sensors and particularly to spectrometers. More particularly, the disclosure pertains to terahertz spectrometers.

SUMMARY

The disclosure reveals a dispersive spectrometer system incorporating terahertz sensitive uncooled sensors.

BRIEF DESCRIPTION OF THE DRAWING

FIG. 11 is an illustrative detector array package; and

DESCRIPTION

Terahertz (THz) spectroscopy may be useful for identifying gases (rotational bands and rotation-vibrational bands) and solids (lattice vibrations). Spectroscopy techniques at THz frequencies may rely on Fourier transform methods (e.g., Michelson or laminar grating spectrometers), time domain spectroscopy (another Fourier transform method), or tunable, narrowband sources.

The system of the present disclosure may show a dispersive slit-based spectrometer using a linear array of uncooled, microbridge detectors, each coupled to its own micro-antenna. The linear array of detectors sensitive at THz frequencies may be integrated into a dispersive slit-based spectrometer having fore-optics, slit aperture, secondary optics, and a dispersive element which reimages the slit onto a detector array. The array of detectors may be designed to have optimum sensitivity in the spectral range of interest defined by the dispersive range of the element. The array may be THz sensitive and uncooled. The array of uncooled THz-sensitive detectors may be used to collect the THz radiation in each spectral bin (sub-band). The system may use the convention that terahertz (THz) radiation includes frequencies of the electromagnetic spectrum typically between 0.1 THz and 10 THz.

A dispersive spectrometer may be realized in several forms using refractive or reflective optics, and one or more of various types of dispersive elements. The dispersive spectrometer may use arrays of detectors (either 1D or 2D) to realize a multiplexing advantage (i.e., the energy in each spectral band may be sampled during the time the spectrum is acquired).

Patent applications owned by the same assignee of the present application may be referred to for additional spectroscopic information. The applications may include U.S. patent application Ser. No. 11/350,541, filed Feb. 9, 2006, and U.S. patent application Ser. No. 11/446,806, filed Jun. 2, 2006. U.S. patent application Ser. No. 11/350,541, filed Feb. 9, 2006, and U.S. patent application Ser. No. 11/446,806, filed Jun. 2, 2006, are hereby incorporated by reference.

Figure 1:
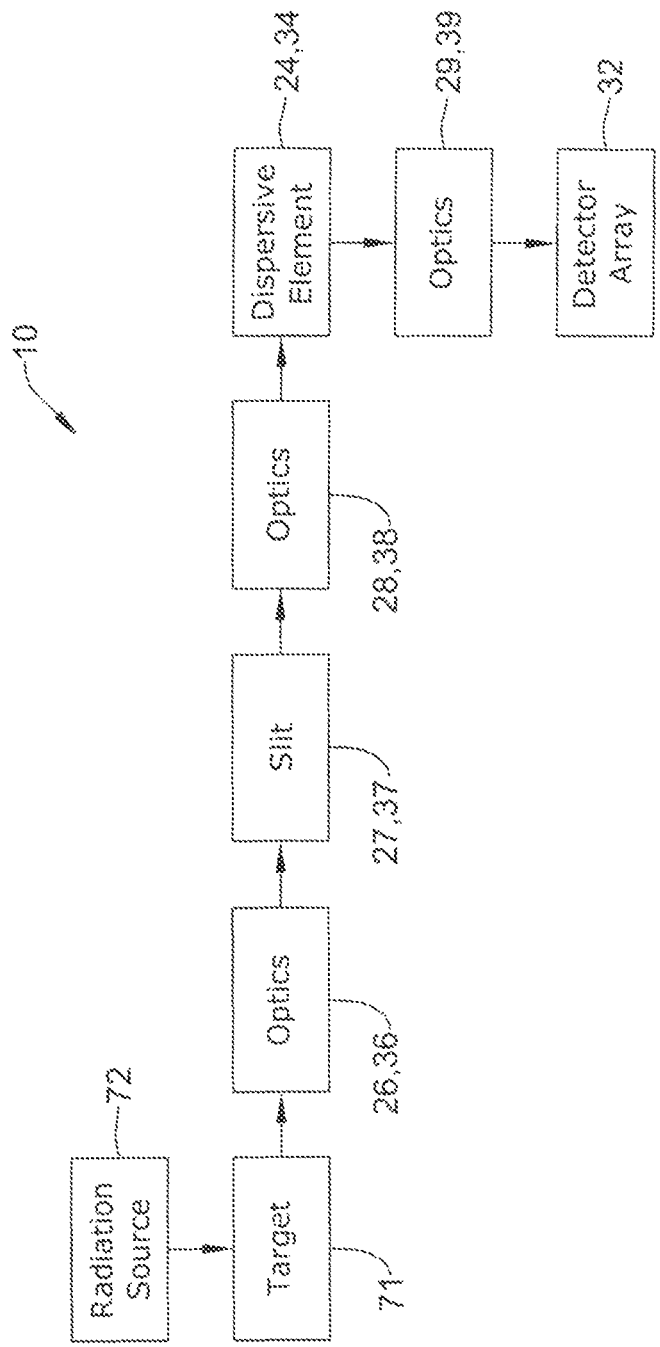
FIG. 1 is a diagram of an overall layout of the present spectrometer system.

FIG. 1 is a diagram of an overall layout of the present spectrometer system 10. There may be a target 71 having a material of interest. Target 71 may be impinged with terahertz radiation from a source 72. Spectrometer system 10 may work with virtually any THz source. However, a blackbody source may be a THz source. For example the blackbody source may be an aqueous blackbody calibration source, such as the one described in "Aqueous blackbody calibration source for millimeter-wave/terahertz metrology" (Dietlein, C., Popovic, Z., & Grossman, E. (2008). See "Aqueous blackbody calibration source for millimeter-wave/terahertz metrology" in *Applied Optics* 47(30), 5604-5615). Target 71 may reflect or emanate radiation, such as light, which includes components having terahertz frequencies. The radiation may go through optics 26, 36. Optics 26, 36 may focus the radiation onto a slit 27, 37. Radiation going through slit 27, 37 may go through optics 28, 38 which collates the radiation. The collated radiation may go to a dispersive element 24, 34. Element 24, 34 may disperse the radiation according to wavelength. Dispersed radiation from element 24, 34 may be focused by optics 29, 39 onto a detector array 32. The optics may be refractive or reflective or a combination of refraction and reflection. There may be other forms of radiation conveyance and control.

Figure 2A:
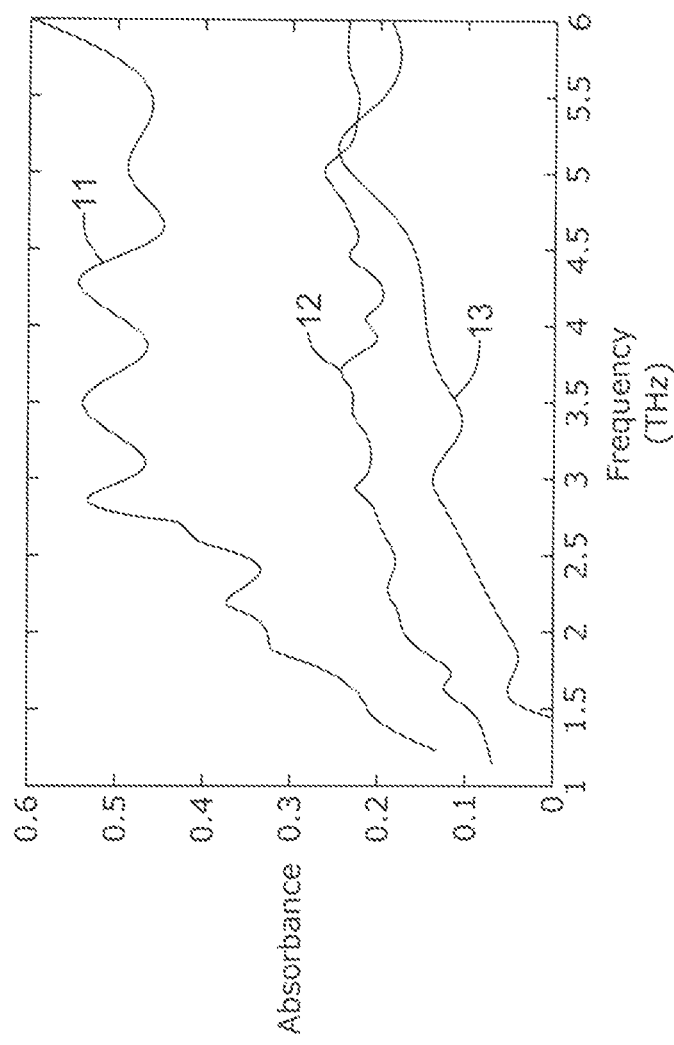
FIGS. 2a-2f are graphs of spectra of various materials.
Figure 2B:
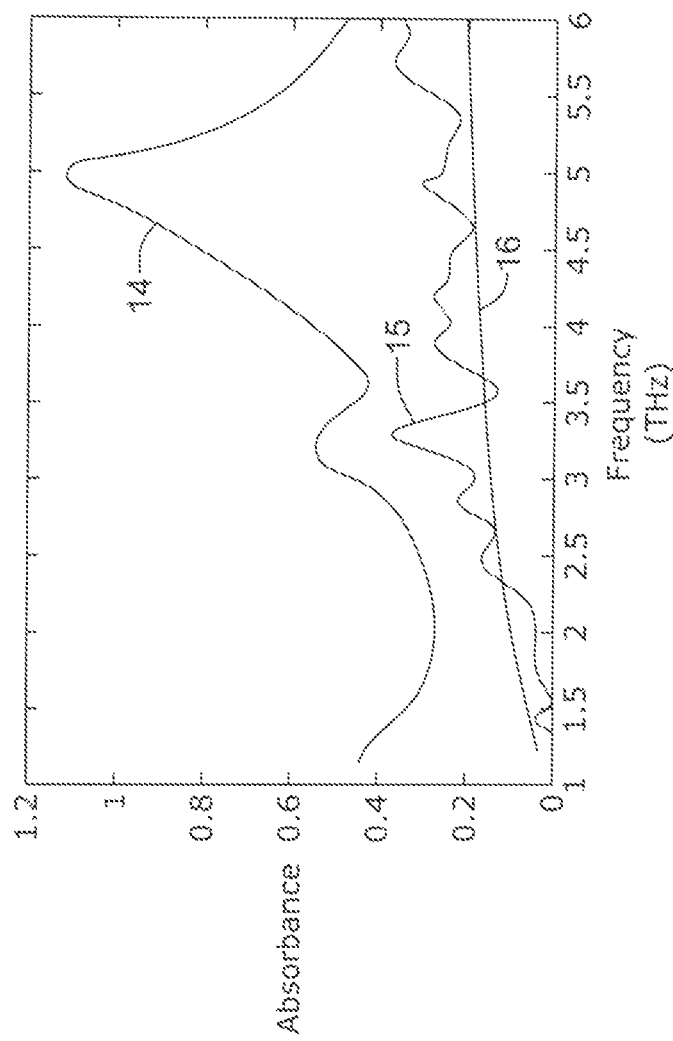
Figure 2C:
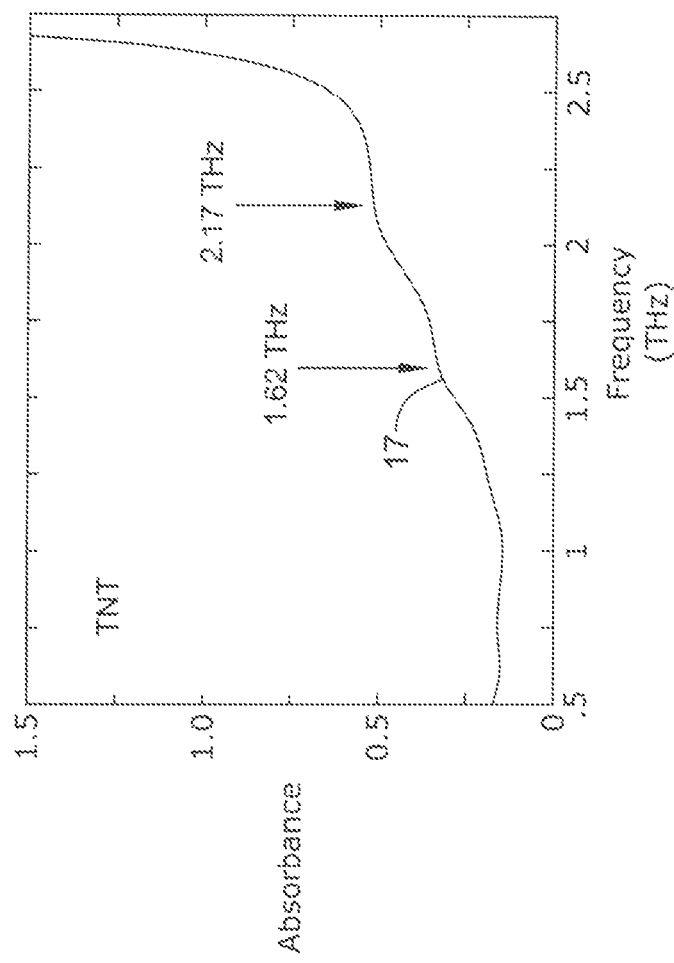
Figure 2D:
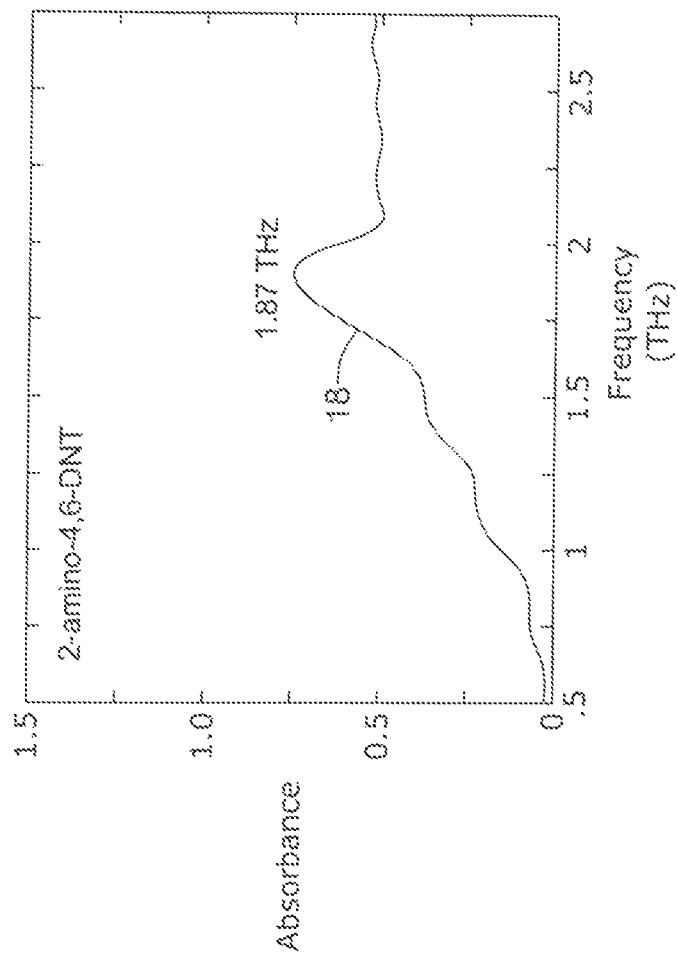
Figure 2E:
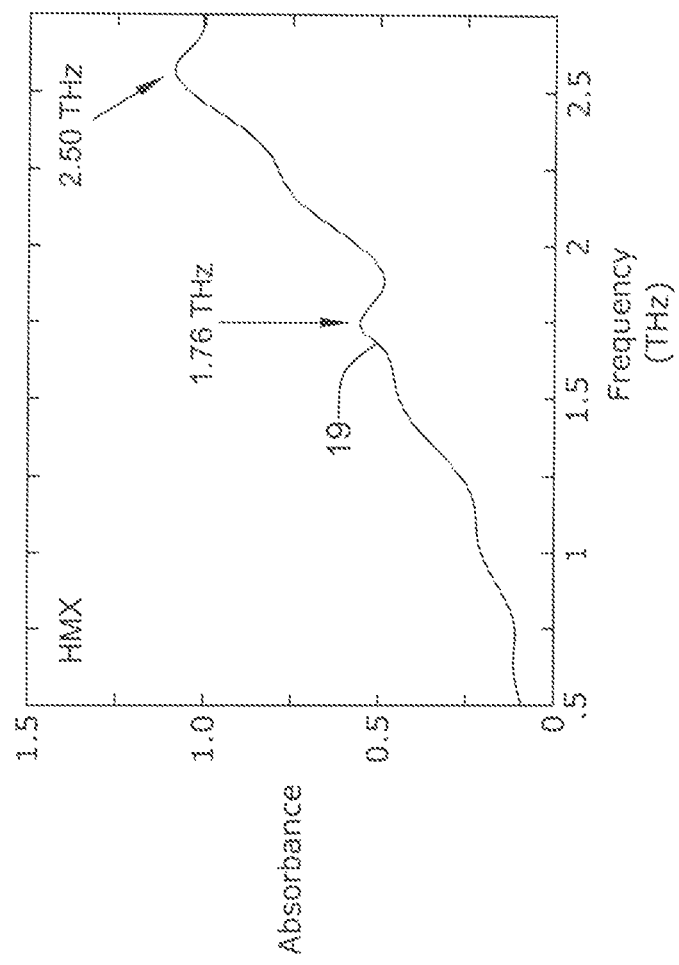
Figure 2F:
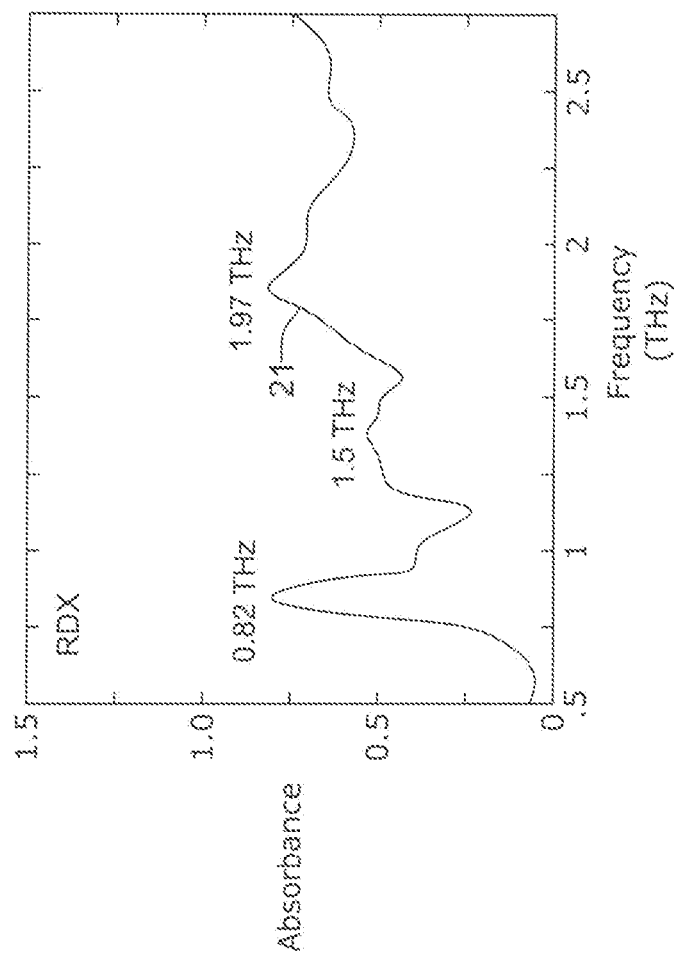

The following figures show an application of the present system. FIGS. 2a-2f illustrate spectral features in a number of crystalline or polycrystalline materials which may be detected with the present system. Rotational bands and rotational-vibrational bands of gases may exhibit spectral features at THz wavelengths. Spectra features may be regarded as rich "fingerprint" features enabling identification of various materials. FIG. 2a shows a graph of absorbance versus frequency (THz) which reveals distinct curves 11, 12 and 13 of pharmaceuticals such as Tylenol™, aspirin and Aleve™, respectively. FIG. 2b shows a graph of absorbance versus frequency (THz) which has curves 14, 15 and 16 of background material such as caffeine, lactose and salt, respectively.

FIGS. 2c-2f reveal an application of the present spectrometer system with absorbance versus frequency curves 17, 18, 19 and 21, respectively, for explosive-related compounds. Identification of these compounds with the curves may impel a critical application of the present system. Frequency peaks of the curves may provide an identification of the compounds. For instance, frequency peaks 1.62 THz and 2.17 THz of curve 17 may be an identification of TNT. Curve 18 has a significant 1.87 THz peak which may be indicative of a 2-amino-4,6-DNT material. Peaks of 1.76 THz and 2.50 THz of curve 19 may indicate HMX. RDX may be identified by 0.82 THz, 1.5 THz and 1.97 THz peaks of curve 21.

Figure 3:
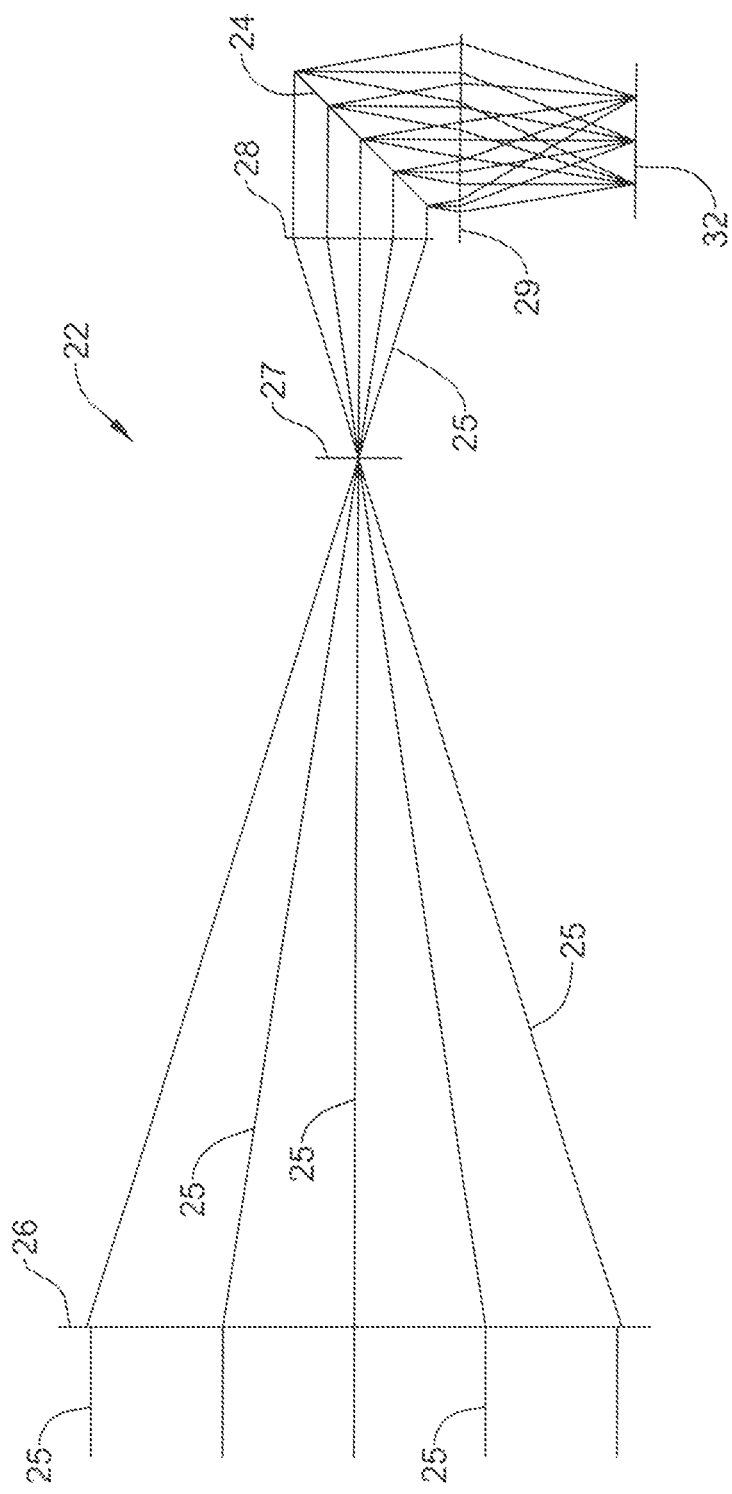
FIG. 3 is a diagram of a spectrometer with refractive optics.
Figure 4:
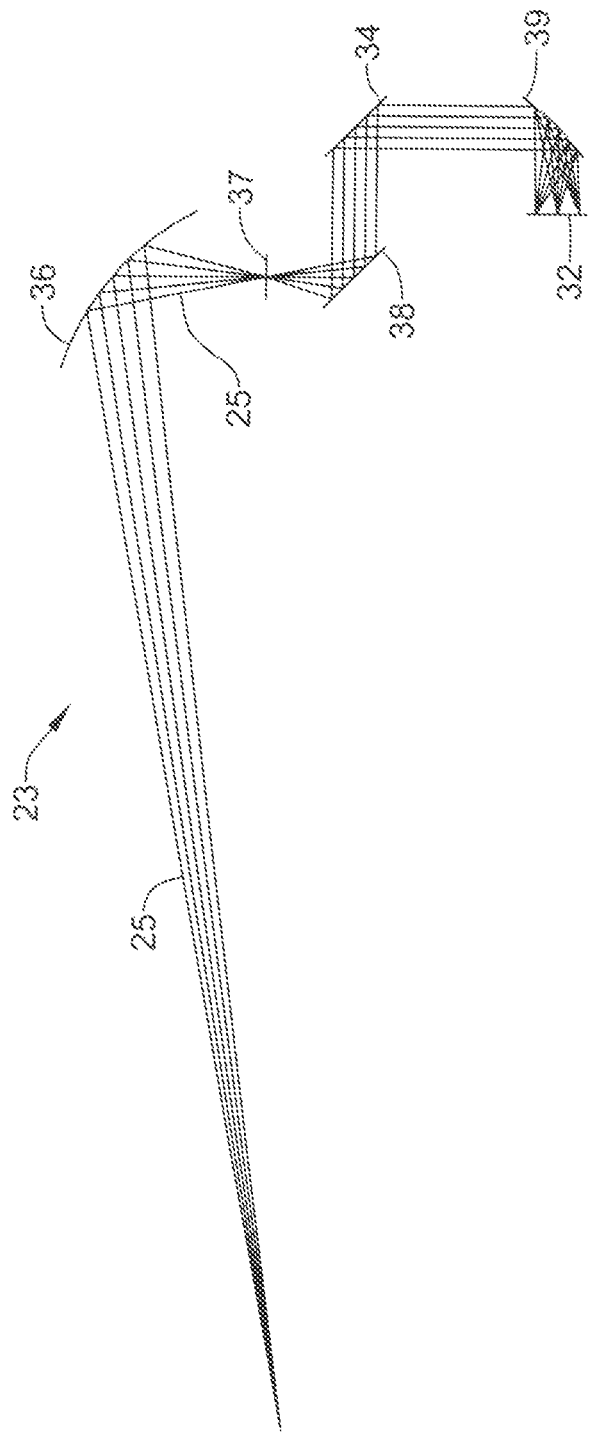
FIG. 4 is a diagram of a spectrometer with reflective optics.

FIGS. 3 and 4 are diagrams of two implementations 22 and 23 of a THz spectrometer having refractive optics and reflective optics, respectively. Radiation 25 being reflected or emitted by a material may be captured by the refractive spectrograph 22. Radiation 25 may be a focused by a fore optic 26 through a slit 27 and onto a collimating lens 28. Collimated radiation 25 from lens 28 may impinge a transmissive dispersive element 24. Dispersive element 24 may be a grating, a prism or a grism (i.e., a combined grating and prism). The dispersive element may instead be reflective. Radiation 25 may be dispersed at different angles from the element 24 according to wavelength of the radiation. The dispersed radiation may be focused by a lens 29 onto a THz detector array 32.

Radiation 25 being reflected or emitted by a material may be captured by the reflective spectrograph 23. Radiation 25 may be a reflected by an ellipsoid reflective element 36 (viz., a fore optic) and focused through a slit 37 and onto a collimating reflective element 38. The collimated radiation 25 may impinge a reflective dispersive element 34. Dispersive element 34 may be a grating, prism or grism. The dispersive element may instead be transmissive. Radiation 25 may be dispersed at different angles from the element 34 according to wavelength of the radiation. The dispersed radiation may be focused by a paraboloid reflector 39 onto the THz detector array 32.

Figure 5:
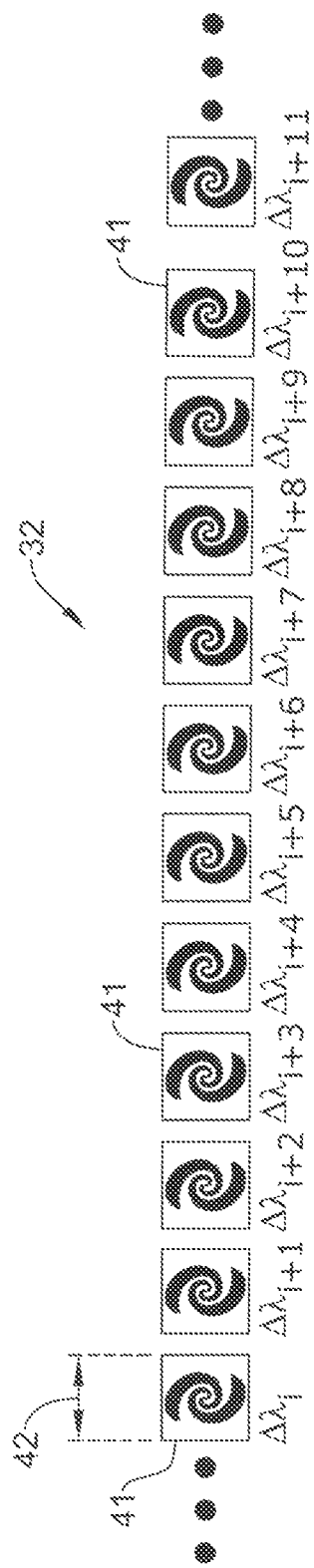
FIG. 5 is a diagram of an array of detectors of the present system.

The detector array 32 may include a linear array of uncooled THz radiation sensitive detectors 41 specific to the present dispersive spectrograph system 22, 23. FIG. 5 is a diagram of array 32 of detectors 41. The spectral sensitivity, including gain and efficiency, of the detectors 41 or subgroups of them, may be adjusted by varying the design of the respective micro antennas of the detectors 41. The detector width 42 may be determined by the wavelength and a size of the image of the slit 27, 37 at the focal plane of the detector 41. The wavelengths for respective detectors 41 may be $\Delta\lambda_i$, $\Delta\lambda_{i+1}$, $\Delta\lambda_{i+2}$, .... Each of these detectors 41 may indicate a given intensity THz signal of the image impinging it. The number of detectors 41 in the array 32 may be determined by the bandwidth desired of the spectrometer.

Figure 6:
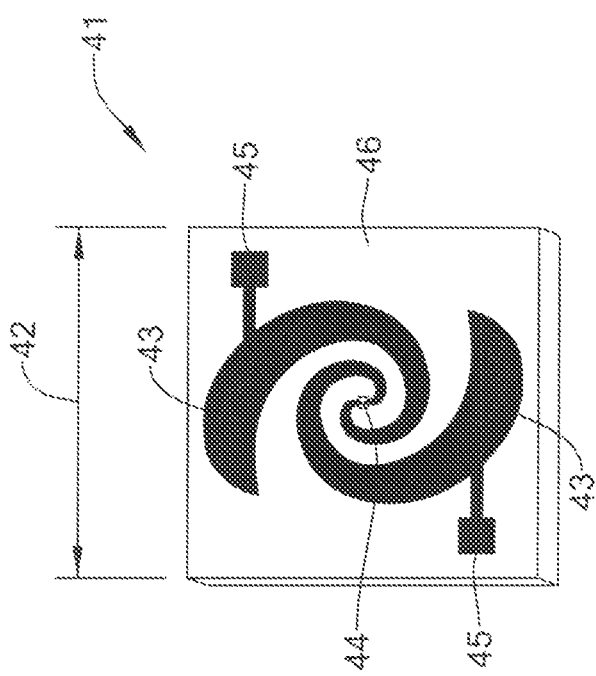
FIG. 6 is a diagram of a terahertz detector.

FIG. 6 is a diagram of design details of a THz detector 41. In some instances, the detector 41 may be a thermoelectric detector. While a thermoelectric detector may require preamplification, thermoelectric detection may provide some benefits over the bolometric method for a THz sensor. For example, the thermoelectric method may provide no 1/f noise under low illumination whereas a bolometer may generate 1/f significant noise. Additionally, thermoelectric detectors may have negligible offsets and drifts, lower electronic power requirements, may be compatible with on-array, pixel-level read-out electronics, and may have higher yield and less costly processing (no $VO_x$ required).

In some cases, the detector may be designed such that the collection of THz radiation is separated from the detection of THz radiation. This may allow the optimization of each function independently. The detector may have micro-antenna elements 43 to collect incident THz radiation. A thermally isolated micro-bridge sensor element 44 may be situated at a central juncture at a gap between antenna element ends. The micro-bridge element 44 may bridge the gap. In some instances, the micro-bridge element may be approximately 1×40 0.3 microns (µm). However, these dimensions are merely illustrative and the micro-bridge may have any size desired. Element 44 may be, for example, a thermoelectric (TE) MEMS micro-bridge. Element 44 may convert the collected THz radiation into an electrical signal. The electrical signal may be read out at pads 45 of each detector 41. Antenna elements 43, along with pads 45, and sensor element 44 may be situated or formed on a membrane 46.

A dimension of length or width 42, which may be of either edge as detector 41 can be square in overall configuration. In some instances, the length or width may be approximately 500-600 µm. Alternatively, the overall configuration and/or outside dimensions may have a geometrical shape different than those as shown in FIGS. 5 and 6. The micro-bridge sensor 44 may be one of several types. Various types of sensors 44 may include those of bolometric, thermoelectric, pyroelectric, ferroelectric, and the like.

The dimension of the length or width 42 of detector 41 may be determined by the spectral band of the radiation that detector 41 is to sense. The dimensions 42 may be in a range of microns, depending on detected frequencies.

Figure 7:
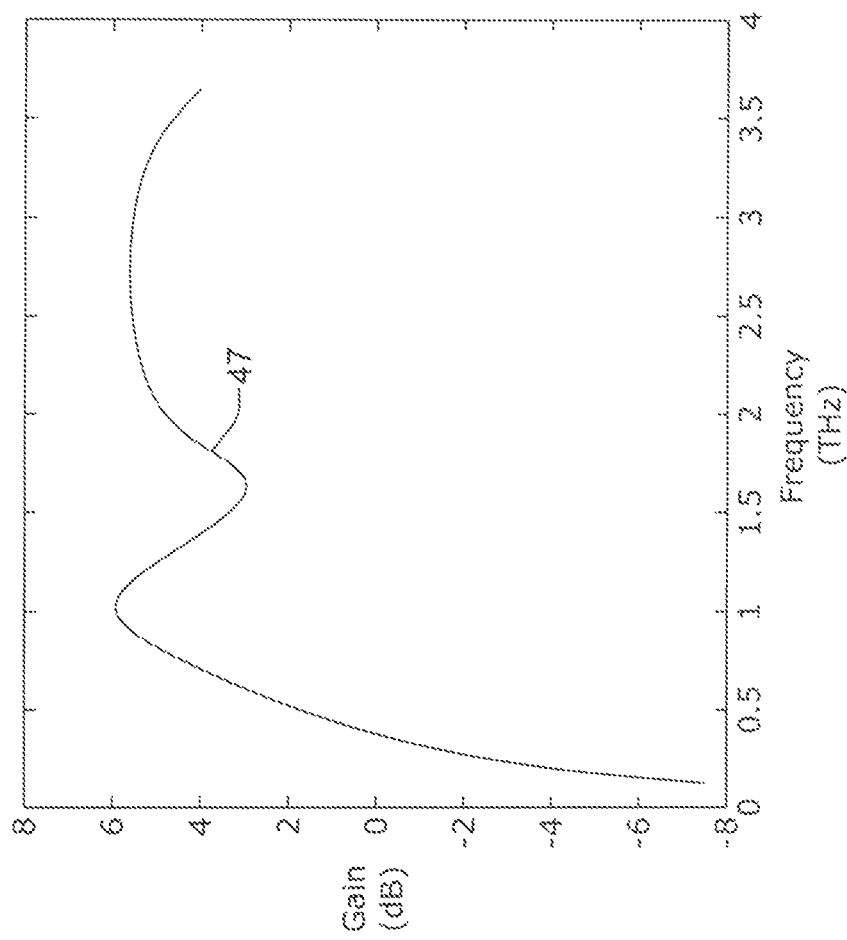
FIG. 7 is a graph of an example bandwidth for a micro-antenna of the terahertz detector.

FIG. 7 shows a graph of an example of bandwidth for a micro-antenna 43 of detector 41. The graph shows a curve 47 of gain (dB) versus frequency (THz) which may represent a micro-antenna gain spectrum for a particular detector 41 having certain dimensions 42, antenna 43 type, sensor 44, and various design parameters.

One of the features of the detector 41 of the present system, which permits it to achieve very high sensitivity without requiring cooling, may include a very significant amount of thermal isolation provided between the collection of the radiation (via the micro antenna 43) and the detection of the radiation (via the microstructure 44). In some instances, the micro antenna arms 43 may be spaced by a distance. For example, the gap between the antenna arms 43 may be approximately 10 µm.

Figure 8:
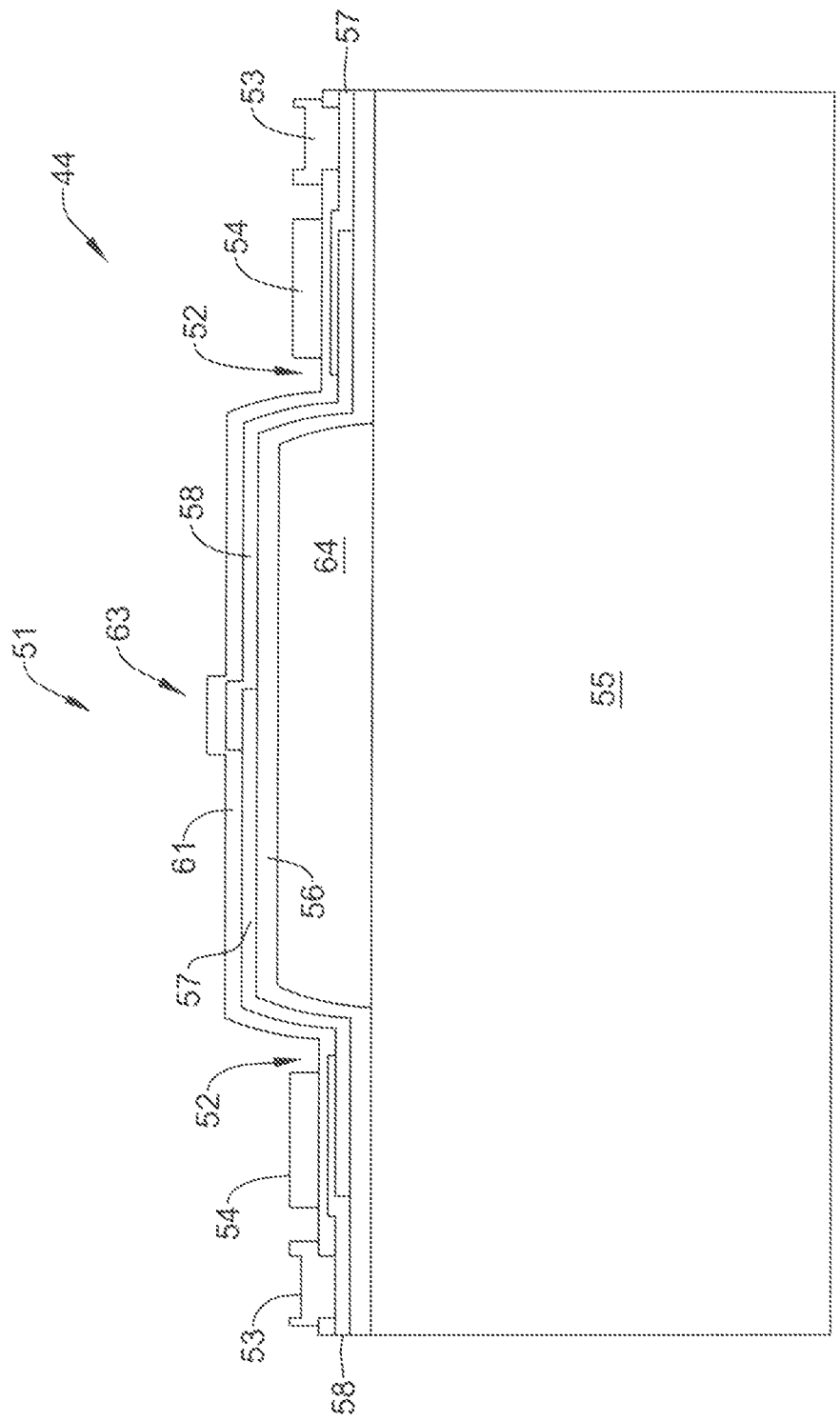
FIG. 8 is a cross-section view of a MEMS thermal electric micro-bridge sensor.

FIG. 8 shows a cross-section view of the TE MEMS microbridge sensor element 44. This view shows a "hot" thermoelectric (TE) junction 63 formed in the center of the detector at the base of a first antenna arm 43, a "cold" TE junctions 52, TE readout points 53, and antenna contacts 54. The components may be fabricated with micro electro mechanical systems (MEMS) technology situated on a substrate 55. The antenna coupling may be capacitive, resistive, or a combination thereof. The micro-bridge element 44 dimensions may be about 50×1×0.2 microns or 40×1×0.3 microns.

The microstructure 44 may have a microbridge 51 suspended on a dielectric membrane 56 over a substrate 55, such as silicon. Microbridge 51 may have a thermocouple 63 situated in the middle. A dielectric layer 56, such as silicon nitride, may be suspended over the substrate 55 by removal of a sacrificial layer in volume 64, and formed to provide the general shape of the microbridge 51. A layer 57 of a first metal, such as nickel iron (NiFe), may be deposited on top of the silicon nitride 56 extending from the mid-portion of the microbridge 51 towards the vicinity of the first antenna contact pad 54 on the left. A layer 58 of a second metal, such as chrome, may be deposited on top of the silicon nitride layer 56 extending from the mid-portion of the microbridge 51 towards the vicinity towards the vicinity of the second antenna contact pad 54 on the right. In the middle of the microbridge, the NiFe layer 57 and the chrome layer 58 may overlap for a short distance. Another dielectric layer 61 may be formed on top of the microbridge 51. The overlapping layers of the two metals (NiFe and chrome) may form a hot thermoelectric (TE) junction 63 of a thermocouple. Cold junctions 52 of the thermocouple may be positioned on the substrate at the ends of the NiFe and chrome layers. At the end of the chrome layer 58, there may be junction 52 by an overlapping NiFe layer 57. At the end of the NiFe layer 57, there may be another junction 52 by an overlapping chrome layer 58. NiFe and chrome are example materials. Other suitable materials may be used for the hot and cold junctions.

Certain properties of the two materials may be selected relative to each other so as to optimize sensor performance. Some properties of interest may include electrical resistivity, thermal conductivity, and the Seebeck coefficient.

The currents caused to appear in the antenna 43 of detector 41 by incident radiation in its detection bandwidth may be coupled to the microbridge 51 of sensor element 44. The current in the microbridge 51 may generate heat in the junction 63. The heat may generate a voltage differential between the hot TE junction 63 on the microbridge and a cold TE junction 52 on the substrate at the foot of the microbridge 51. The voltage generated may be proportional to the product of the Seebeck coefficient (61 μV/K) and the temperature difference of the junctions 63, 52. A voltage differential may appear at the contact pads 53 to which the read-out electronics can be coupled. The electronics may be on the same die as the micro antenna and microstructure. Alternatively, the readout electronics may be embodied on a separate die.

The antenna contact pads 54 may have a coupling mechanism between the micro antenna and the microstructure, and the thermocouple may have a "temperature signal detector". The microbridge 51 as a whole may essentially include the hot 63 and the cold 52 TE junctions. The microstructure 44 may include the silicon nitride layer 56 which is suspended above the substrate and upon which the metal layers 57 and 58 and hot thermocouple junction 63 are supported.

The thermocouple 63, e.g., a temperature signal detector, may be well thermally isolated from the substrate 55 and the outside world by virtue of being in the middle of the microbridge 51 and most distant as practical from the substrate 55. Accordingly, much of the heat generated in the microbridge 51 may go to raising the temperature of the NiFe 57 and chrome 58 layers and will not be lost in the substrate 55. While the thermocouple 63 may be in ohmic contact with substrate 55, thermal conductance between microbridge 51 and substrate 55 is de minimis.

A gap between the micro-antenna arms 43 may limit the upper frequency response of the detector, which may be generally expressed as:

$$\text{Gap} \ll \lambda/10$$

Figure 8A:
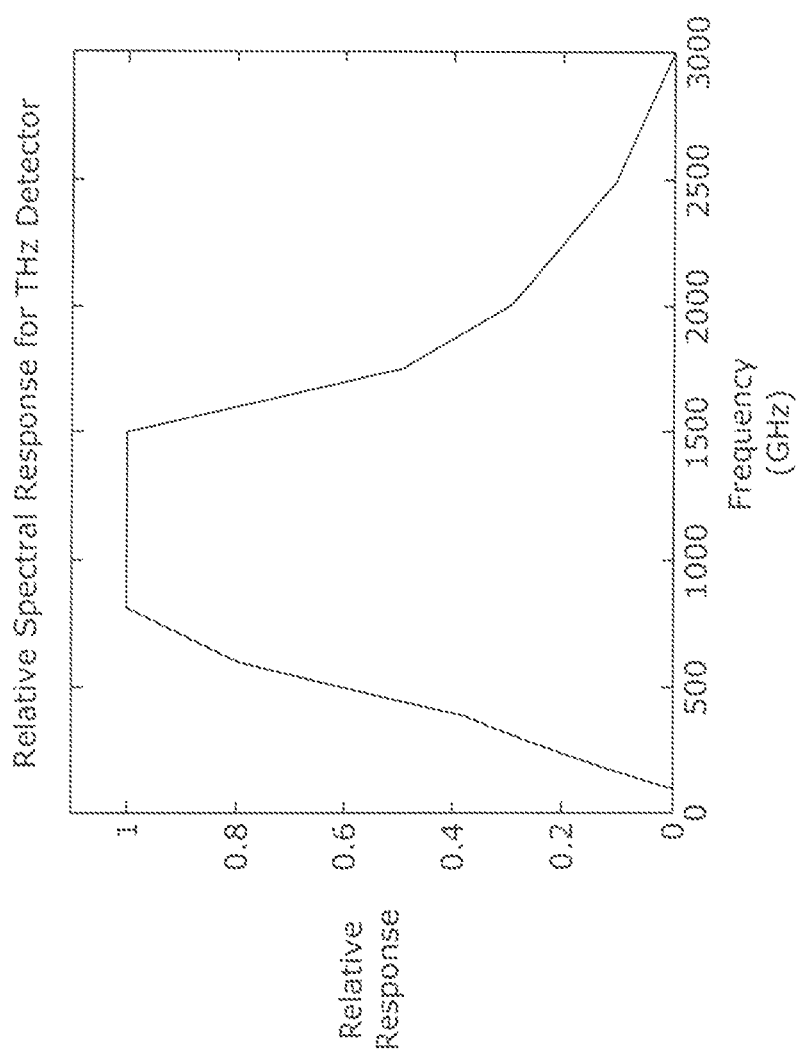
FIG. 8A is a graph of an example relative spectral response for a THz detector.

For example, a detector having a gap of 10 μm between the antenna arms may limit the detector's responsivity to frequencies less than 3 THz (100 μm). At lower frequencies, the spectral response may be governed by the arm length, impedance matching to the microbridge and surroundings, and the presence of a backplane. In some instances, the detector may not have backplanes in order to maximize the spectral bandwidth. FIG. 8A illustrates a relative spectral response for a THz detector having a 500 μm arm and a 40×1×0.3 μm microbridge element. Measurements were performed both with a tunable backward-wave oscillator in range 180 GHz to 850 GHz and with a lamellar grating interferometer and 900K blackbody source for the range 800 GHz-3 THz. As can be seen, the detector may have a non-zero response over a frequency range of 100 gigahertz (GHz) to 3 THz.

In some instances, noise contributions may arise from the thermoelectric detector and an accompanying preamplifier (not explicitly shown in the Figures). Johnson noise in the microbridge resistance may be the dominant noise source for the detector. However, in some instance, radiation noise and thermal noise may be present, but may be several orders of magnitude smaller than the Johnson noise. As discussed above, 1/f noise may not be present. The resistance of the microbridge may be approximately 195-250 ohms (Ω).

The radiometric responsivity of a micro-antenna-coupled TE detector may be given by the simple expression:

$$R = \eta S/G$$

where η is the power coupling efficiency of the micro-antenna to the microbridge, S is the Seebeck coefficient (61 μVolts/Kelvin in some instances), and G is the net thermal conductance for the microbridge (approximately 2×10−7 Watts/Kelvin). The maximum value for the coupling efficiency η is 0.5 when the micro-antenna is impedance matched to the microbridge and is purely resistive over the spectral bandwidth of the detector. Assuming perfect impedance matching, for the detector of FIG. 8A, the predicted radiometric responsivity without a backplane is 152V/W (the value is approximately double with a backplane, at the cost of a smaller spectral bandwidth). Measurement of this radiometric responsivity is nontrivial, and an estimate of ~110V/W was obtained. Using this value with the measured noise, a noise-equivalent power (NEP) for the detector alone may be approximately 13 pW/√Hz, or approximately 16 pW/√Hz for the detector and preamplifier together. The predicted values (without backplane) are 9.4 pW/√Hz and 11.6 pW/√Hz, respectively.

Figure 9:
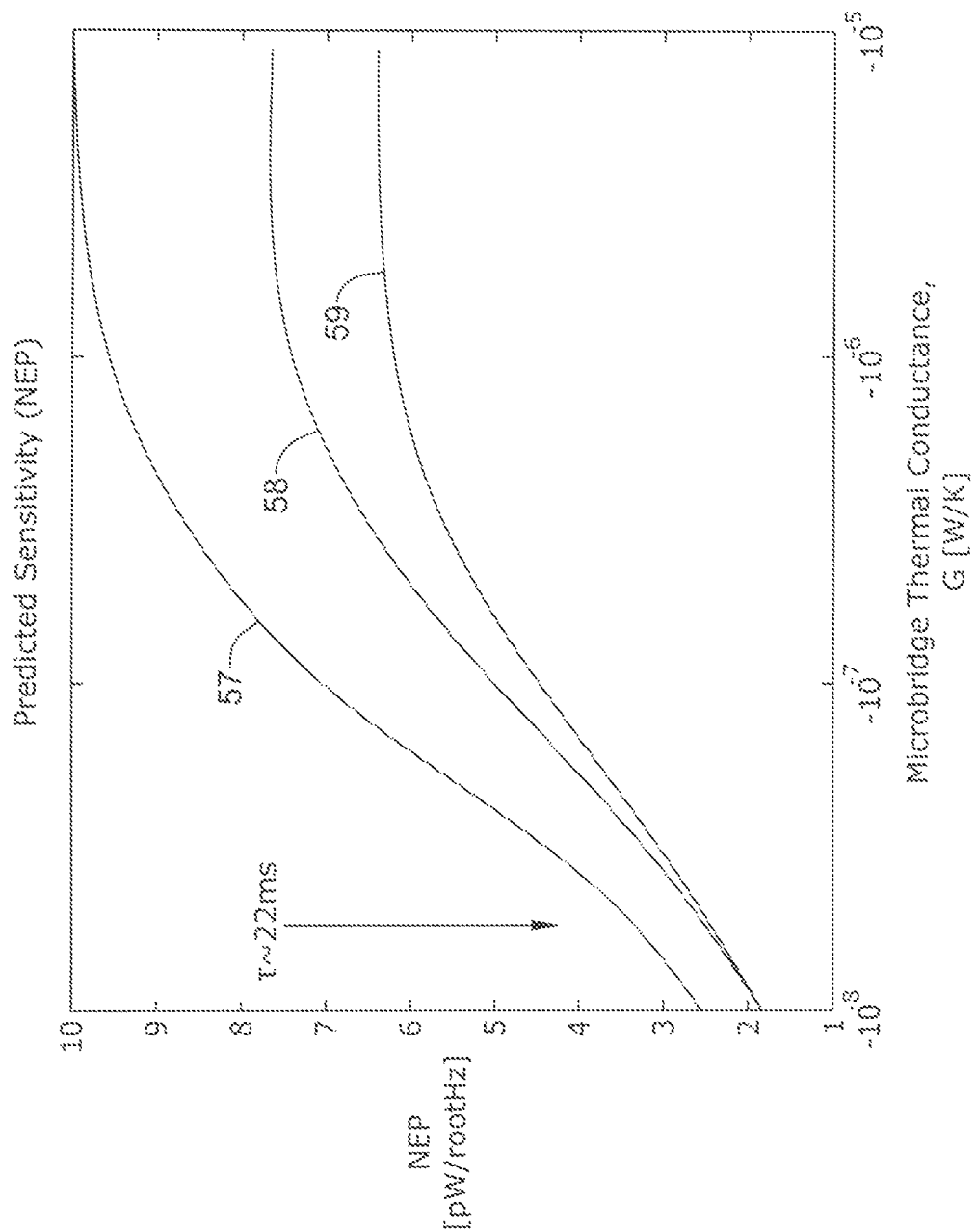
FIG. 9 is a graph of noise equivalent power versus thermal conductance of an uncooled thermoelectric microbridge sensor.

FIG. 9 illustrates sensitivity in terms of noise equivalent power (NEP) for a typical uncooled THz thermoelectric detector 41 with typical readout electronics. The Figure shows a graph of NEP (sensitivity in pW/root Hz) versus micro-bridge thermal conductance, G (W/K). Curve 57 reveals the total sensitivity of the detector 41 and associated electronics. The time constant τ (tau) of the response may be noted to be about 22 milliseconds. The electronics may be an ultra low distortion and ultra low noise operational amplifier AD797 by Analog Devices, Inc. Curves 58 and 59 of the graph reveal the sensitivity of the detector and the electronics, respectively.

Figure 10A:
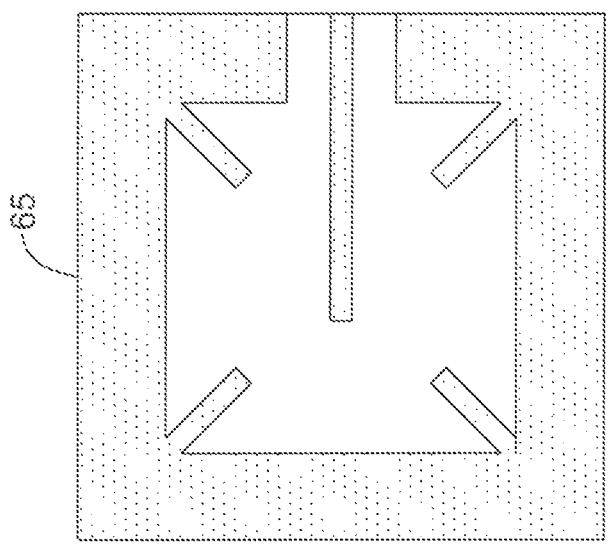
FIGS. 10a, 10b and 10c are diagrams of several micro-antennas that may be used in the present terahertz detector.
Figure 10B:
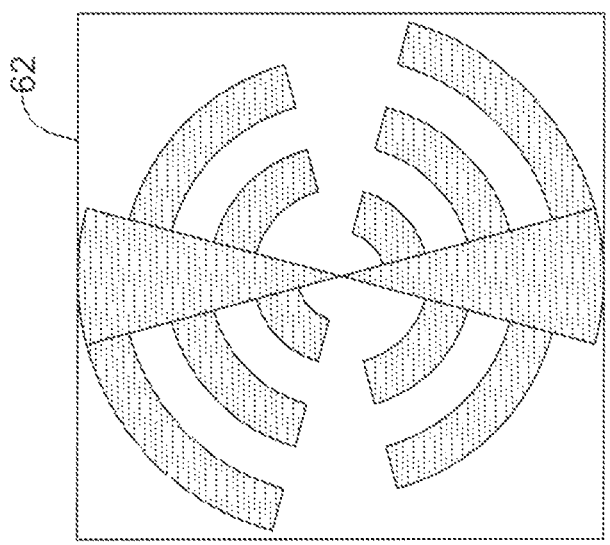
Figure 10C:
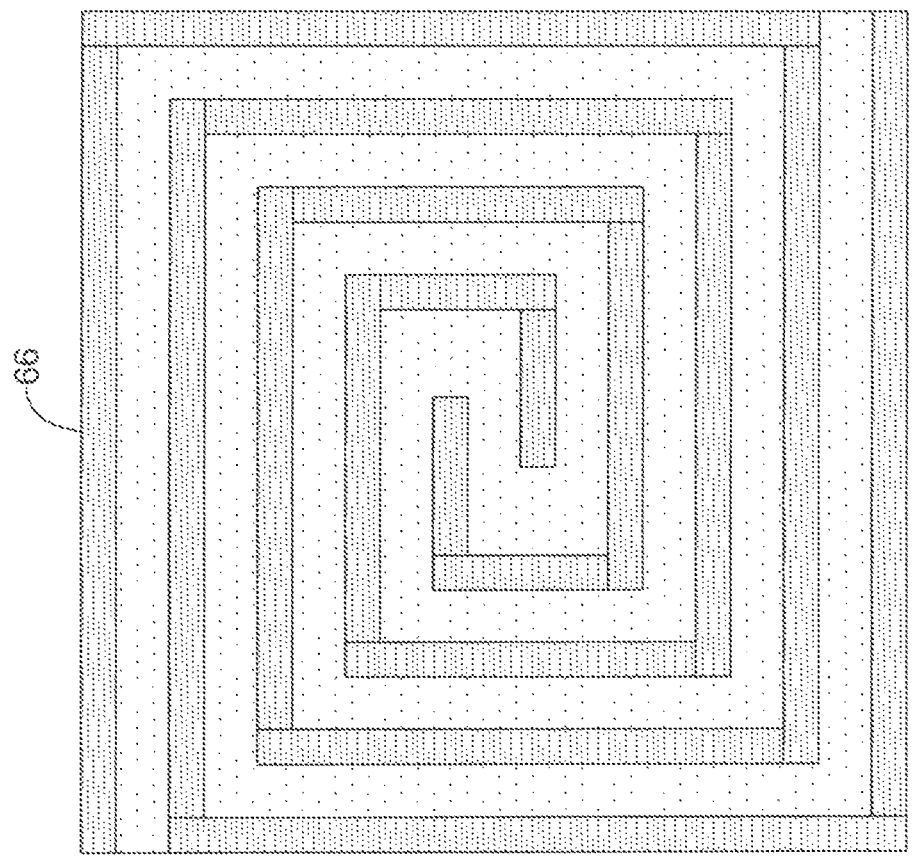

FIGS. 10a, 10b and 10c reveal other micro-antenna options, besides the micro-antenna 43 for detector 41 in FIGS. 5 and 6. Antenna type 65 is shown as a square slot with a simple, low risk detector coupling capability. It may have a gain of about 5±0.7 dB and a bandwidth of 1.5 to 2.5 THz. The polarization sensitivity of antenna type 65 may be regarded as independent.

Antenna type 62 is shown as a log periodic with a simple resistive coupling or a less simple capacitive coupling. It may have a gain of about 5±0.7 dB and a bandwidth of 1.3 to 2.7 THz. The polarization sensitivity of antenna type 62 may be regarded as dependent.

Antenna type 66 is shown as a spiral with a simple resistive or less simple capacitive coupling. It may have a gain of about 7±0.5 dB and a bandwidth of 0.5 to 3.0 THz. The polarization sensitivity of antenna type 66 may be regarded as independent.

In some instances, the THz detectors may be fabricated as 1×4 arrays and packaged as 1×8 linear arrays integrated with preamplifiers in a hermetic vacuum package sealed with an antireflective silicon window (90% transmittance). FIG. 11 illustrates a detector array package 100 including two 1×4 arrays 105 to form a 1×8 array of detectors. While not explicitly shown the detector package 100 may further include a silicon window. The detector package 100 may further include a plurality of low noise preamplifiers 110.

Figure 12:
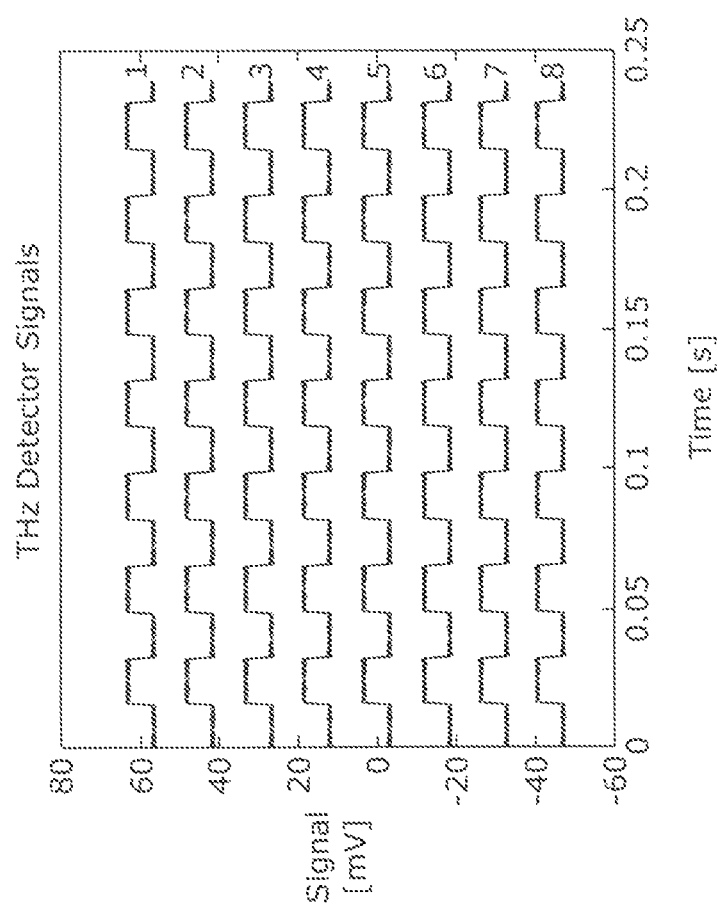
FIG. 12 is a graph of an example signal from the illustrative detector array package of FIG. 11.

In some applications, noise equivalent differential temperature (NEΔT) may be a more relevant figure-of-merit and may be more straight-forward to measure than NEP. FIG. 12 illustrates the chopped signals from all eight detectors (shown in FIG. 11) illuminated by a 900K blackbody source imaged on the detectors with an f/1.1 matched pair of off-axis paraboloids (1× magnification). The detector signal may be measured directly as the amplitude of the chopped waveform, and the noise may be extracted from the variation within each flat region of the waveform. These values are recorded along with the signal-to-noise ratio (SNR) and the microbridge resistance. With two additional inputs, the preamplifier-detector noise bandwidth and the angular distribution of the blackbody source, the NEΔT may be extracted from this data. The measured NEΔT value may be calculated using the following equation:

$$NE\Delta T_{model}(30\ Hz) = \frac{\Delta T_{EE}}{\alpha \cdot SNR}\sqrt{\Delta f}$$

where $\Delta T_{BB}$ is the measured change in temperature, $\alpha$ is the blackbody vignetting correction factor (1.47), SNR is the signal to noise ratio, and $\Delta f$ is the change in noise frequency. Scaling the SNR from the measured noise bandwidth of 6000 Hz to 15 Hz appropriate for a 30 Hz frame rate with a staring sensor, a value of 1.0K for the NEΔT may be arrived at, after correcting the measured value of 0.8K for direct IR heating of the microbridge. The predicted value is 0.54K, using the measured NEP and taking the spectral bandwidth to be 0.2-2.0 THz with uniform detector response and an atmospheric transmittance calculated for the measurement conditions (0.5 m path in 50% relative humidity at 296K and 1 atmosphere pressure). The predicted value may be obtained by the following equation:

$$NE\Delta T_{model}(30\ Hz) = \frac{NEP\sqrt{\Delta f}}{\tau_{opt}A_{det}\Omega_{proj}\int_{\Delta\nu}\tau_{atm}(\nu)\frac{2k_E}{c^2}\nu^2 d\nu}$$

where NEP is the noise equivalent power, $\tau_{opt}$ is 0.8, $A_{det}$ is $3.6\times10^{-3}$ cm$^2$, $\Omega_{proj}$ is the f/1.1, $\tau_{atm}$ is 0.5 based on 50% relative humidity and 296 Kelvin (K), $k_B$ is Boltzmann's constant, c is the speed of light, $v_1$ is 0.2 THz, and $v_2$ is 2.0 THz.

In the present specification, some of the matter may be of a hypothetical or prophetic nature although stated in another manner or tense.

Although the present system has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A non-imaging dispersive spectrometer system comprising:
    a terahertz radiation source for illuminating a target;
    a slit aperture;
    fore-optics configured to focus incident radiation reflected or emanated from the target to the slit aperture
    a dispersive element;
    secondary optics configured to collimate the radiation from the slit aperture to the dispersive element; and
    one or more thermoelectric terahertz detectors in an optical path from the dispersive element, the one or more detectors each comprising an uncooled, thermally isolated sensor and a micro antenna connected to the uncooled sensor;
    wherein the one or more detectors are arranged according to their optimal sensitivity in a spectral range of interest as defined by the dispersive range of the dispersive element and the one or more detectors form a linear array; and
    wherein the thermally isolated sensor of the one or more thermoelectric terahertz detectors comprises:
    a microbridge, the microbridge comprising:
        a first dielectric layer;
        a first metal layer extending from a mid-portion of the microbridge to a first antenna contact pad;
        a second metal layer extending from the mid-portion of the microbridge to a second antenna contact pad and overlapping a portion of the first metal layer; and
        a second dielectric layer disposed over the first metal layer and a second metal layer.

2. The system of claim 1, wherein the sensor is a thermoelectric MEMS microbridge sensor.

3. The system of claim 1, wherein the terahertz radiation source comprises a blackbody radiation source.

4. The system of claim 1, wherein at least one size dimension of the micro antenna at least partially determines a wavelength to which the microbridge sensor is sensitive.

5. The system of claim 1, further comprising a lens for focusing radiation dispersed according to wavelength from the dispersive element to the one or more detectors.

6. The system of claim 5, wherein the fore-optics, the secondary optics, and the lens comprise distinct sets of optics.

7. The system of claim 1, further comprising:
    processing electronics connected to the one or more detectors; and
    wherein the processing electronics is for receiving THz detection signals from the plurality of detectors and portraying information from the signals as absorbance versus frequency data.

8. The system of claim 7, wherein the processing electronics is further for identifying a material that has properties which correlate with the absorbance versus frequency data.

9. The system of claim 1, wherein the non-imaging dispersive spectrometer system is configured to provide a spectrum of a gas over a range of frequencies.

10. The system of claim 1, wherein the THz radiation ranges from about 0.1 THz to about 10 THz.

* * * * *